United States Patent [19]

Bradley

[11] 4,239,853
[45] * Dec. 16, 1980

[54] ANTIBIOTIC TESTING METHOD AND APPARATUS HAVING A CHANNELIZED RESERVOIR

[76] Inventor: Rex L. Bradley, 6620 Manor Rd., Austin, Tex. 78751

[*] Notice: The portion of the term of this patent subsequent to Feb. 28, 1995, has been disclaimed.

[21] Appl. No.: 5,351

[22] Filed: Jan. 22, 1979

[51] Int. Cl.³ .................. C12Q 1/20; C12M 1/20
[52] U.S. Cl. .................... 435/33; 422/61; 422/72; 435/30; 435/301
[58] Field of Search ............ 435/32, 33, 29, 30, 435/34, 293, 297, 298, 299, 300, 301; 422/61, 72

[56] References Cited

U.S. PATENT DOCUMENTS

| | | | |
|---|---|---|---|
| 507,870 | 10/1893 | Young | 141/239 |
| 3,234,107 | 2/1966 | Kaufman et al. | 195/139 |
| 3,272,719 | 9/1966 | Avakian | 195/103.5 |
| 3,476,515 | 11/1969 | Johnson et al. | 422/61 X |
| 3,532,470 | 10/1970 | Rochte | 422/61 |
| 3,649,464 | 3/1972 | Freeman | 195/140 |
| 3,713,985 | 1/1973 | Astle | 195/103.5 R |
| 3,728,228 | 4/1973 | Duranty | 195/127 |
| 3,759,666 | 9/1973 | Hill, Jr. | 23/230 B |
| 3,826,717 | 7/1974 | Gilbert et al. | 195/103.5 R |
| 3,829,223 | 8/1974 | Hamel | 356/246 |
| 3,832,532 | 8/1974 | Praglin et al. | 195/103.5 R X |
| 3,837,746 | 9/1974 | Acker et al. | 356/201 |
| 3,854,883 | 12/1974 | Montagnon | 23/259 X |
| 3,873,217 | 3/1975 | Anderson et al. | 356/246 |
| 3,876,377 | 4/1975 | Cingualbre | 23/259 X |
| 3,876,378 | 4/1975 | Montagnon | 23/259 X |
| 3,895,661 | 7/1975 | Praglin et al. | 23/259 X |
| 3,925,166 | 12/1975 | Blume | 195/139 |
| 3,936,356 | 2/1976 | Janin | 195/103.5 R |
| 4,076,592 | 2/1978 | Bradley | 435/33 |

*Primary Examiner*—Robert J. Warden
*Attorney, Agent, or Firm*—Arnold, White & Durkee

[57] ABSTRACT

An apparatus for testing the effects of an antibiotic of chemical on a bacterial or biochemical substance of the type having a plurality of side-by-side test chambers each separated from the other by a side wall and having a common reservoir disposed adjacent each test chamber and separated therefrom by a barrier having a height less than the height of each side wall is characterized by an array of guide walls disposed in the reservoir, each guide wall merging into one of the side walls and cooperating with next-adjacent guide wall to define an array of channels. Each channel communicates with one of the test chambers and each channel is adapted to conduct a liquid disposed in the reservoir into the test zone with which it is associated upon rotation of the apparatus about an axis of rotation.

21 Claims, 6 Drawing Figures

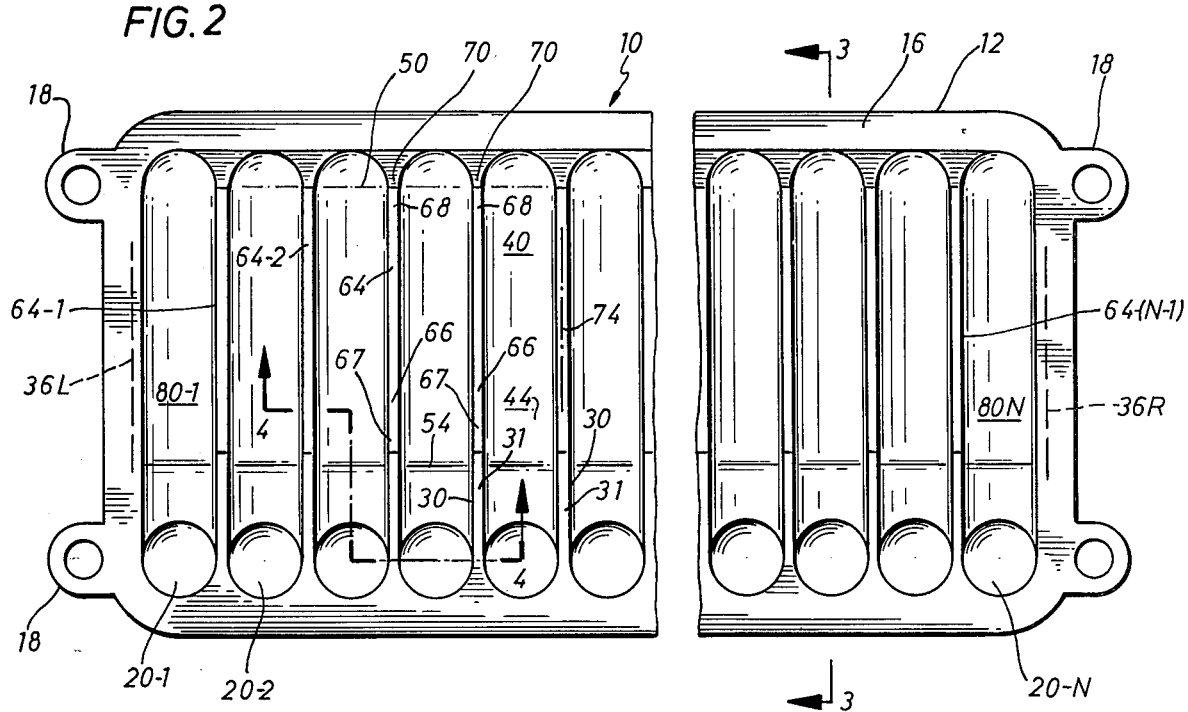
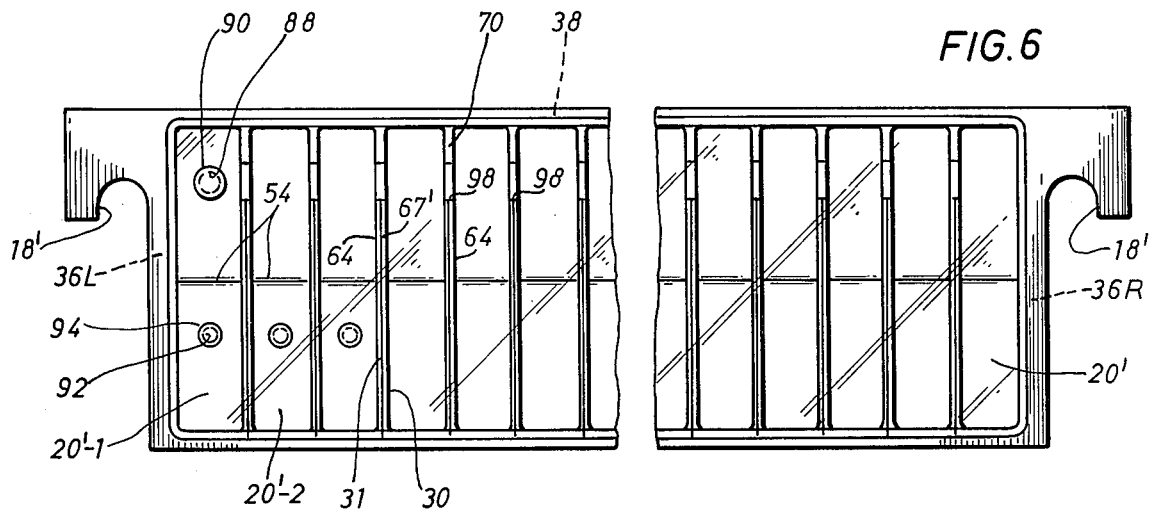
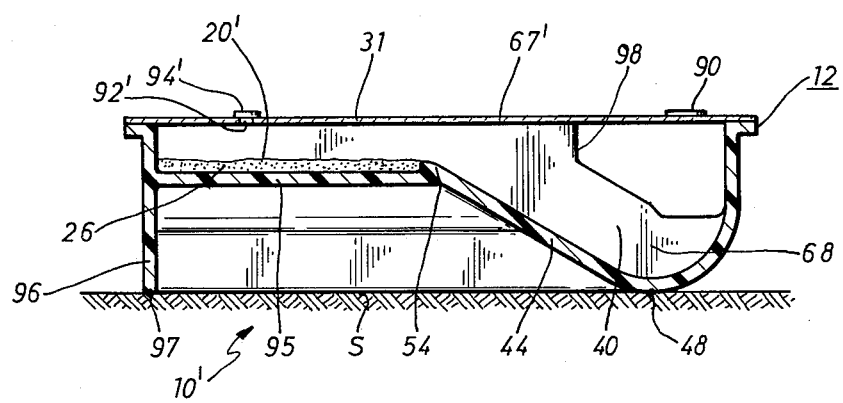

ANTIBIOTIC TESTING METHOD AND APPARATUS HAVING A CHANNELIZED RESERVOIR

BACKGROUND OF THE INVENTION

1. Field of the Invention

This invention relates to apparatus for testing a chemical and more particularly to an apparatus for testing the effect of an antibiotic on bacterial or biochemical substances.

2. Description of the Prior Art

U.S. Pat. No. 4,076,592 issued to the present applicant discloses and claims a method and apparatus for testing the effect of an antibiotic on a liquid suspension of a bacterial or a biochemical substance. Basically, the apparatus disclosed and claimed in the referenced patent includes a reservoir carried by a substantially planar base, the reservoir being separated by a barrier from each of a plurality of side-by-side test chambers also carried by the base. Each test chamber has an antibiotic or biochemical substance disposed therein, and each test chamber is separated from the next-adjacent test chamber by a side wall having a height greater than the height of the barrier. A clear plastic cover is provided to enclose the reservoir and the test chambers so that fluid communication is permitted only between each individual test chamber and the reservoir through a clearance space defined between the interior of the cover and the top of the barrier.

After introduction of a liquid suspension containing the substance to be tested within the reservoir, the method of testing the antibiotic includes the rotation of the apparatus about an axis of rotation parallel to or coincident with an axis extending longitudinally through the reservoir to permit the substance being tested to enter into each of the test chambers from the common reservoir through the clearance defined between the top of each barrier and the interior of the cover. In this manner, the necessity of introducing the substance to be tested into each of the test zones is avoided. Of course, the effect of any chemical substance on any other chemical substance may be tested utilizing the apparatus and method of the referenced patent and this application.

Although the apparatus disclosed in U.S. Pat. No. 4,076,592 is advantageous in that it obviates the need for introduction of the substance be tested individually into each of the test chambers, it appears that care must be exercised during the rotation of the apparatus in order to insure that the substance to be tested is introduced over the barrier from the reservoir into each of the test chambers. It has been observed that any inadvertent tilting or canting of the apparatus during the rotative step may result in the substance not being introduced into certain of the test chambers. This result follows due to the natural tendency of the liquid to respond to the inadvertant tilt of the apparatus by collecting adjacent one end thereof. Thus, during rotation, certain of the test chambers may not receive the liquid suspension of bacteria under test, and the substances in those chambers would not be exposed thereto.

It would therefore appear to be of advantage to provide an apparatus for the testing of a liquid having a chemical substance therein wherein the common reservoir of the apparatus includes an array of guide walls disposed so as to define a channel associated with each test chamber such that the tendency of the liquid to flow to one end of the apparatus in response to inadvertent tilting during the rotative step is avoided and such that the liquid flow is channelized from the reservoir into each test chamber.

SUMMARY OF THE INVENTION

This invention relates to an apparatus and method for testing the effects of a bacterial or biochemical substance suspended in a liquid on a variety of antibiotic or bacterial or biochemical substances, which apparatus is the type having a plurality of side-by-side test chambers each adapted to receive therein an antibiotic or a bacterial or biochemical substance, each test chamber being separated from the next-adjacent test chamber by a side wall of a first predetermined height measured from a given datum. A common reservoir is disposed next-adjacent to and in fluid communication with each of the test chambers, the reservoir being separated from the test chambers by a barrier having a height measured from the same datum that is less than the height of the side walls. An array of guide walls is disposed within the reservoir, each guide wall merging into one of the side walls and cooperating with its next-adjacent guide wall to define an array of channels. Each channel so defined communicates with one of the test chambers.

In operation, a liquid suspension containing the bacterial or biochemical substance to be tested is introduced into the common reservoir to a predetermined level just overlying the lower end of each guide wall. The testing apparatus may then be rotated about a given axis of rotation. The channels conduct the liquid disposed in the reservoir into the test chambers such that if the apparatus is tilted during the rotation, the natural tendency of the liquid to seek its own level at one end of the apparatus is overcome by the action of the guide walls and liquid is channelized and conducted by the channels into each test chamber.

BRIEF DESCRIPTION OF THE DRAWINGS

The invention may be more fully understood from the following detailed description thereof, taking in connection with the accompanying drawings, which form a part of this application and in which:

FIG. 2 is a plan view of the testing apparatus shown in FIG. 1;

FIG. 5 is a side elevational view, in section, showing a modified embodiment of the invention; and FIG. 6 is a plan view of the modified embodiment of the invention.

DESCRIPTION OF THE PREFERRED EMBODIMENT

Figure 1:
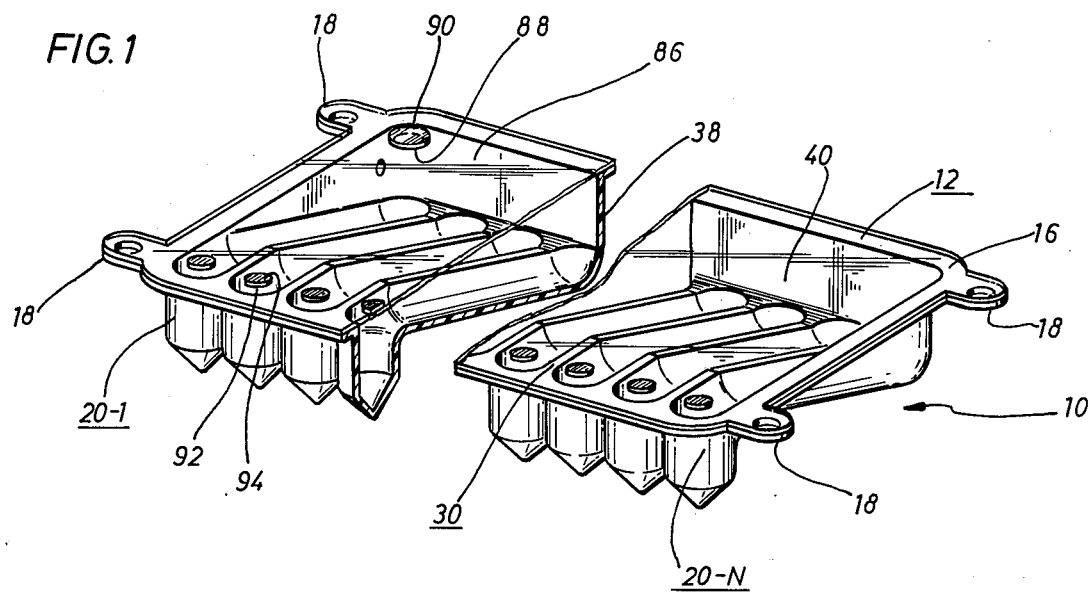
FIG. 1 is a perspective view of an apparatus for testing the effects of an antibiotic on a bacterial biochemical substance embodying the teachings of this invention.

Throughout the following description similar reference numerals refer to similar elements in all Figures of the drawings.

Figure 3:
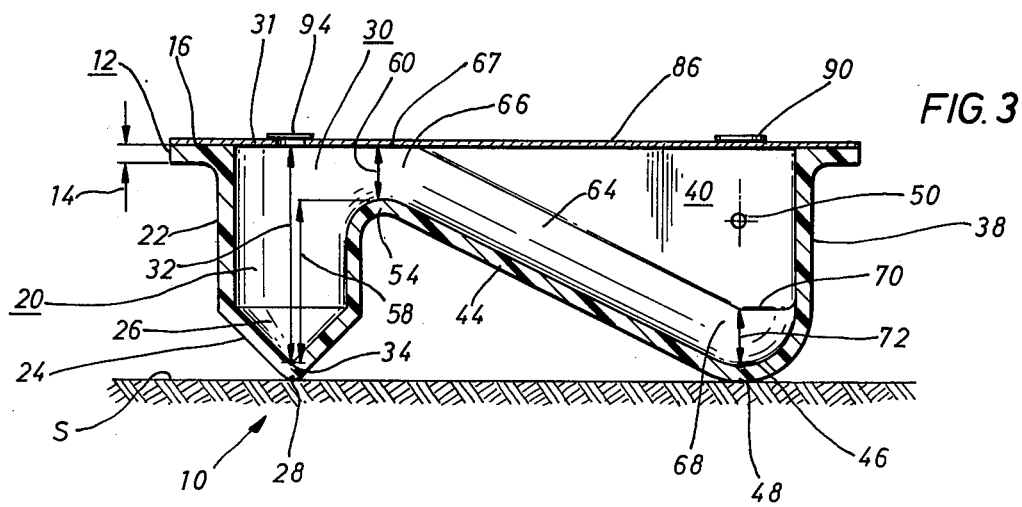
FIG. 3 is a side elevation view of the apparatus taken along section lines 3—3 in FIG. 2.
Figure 4:
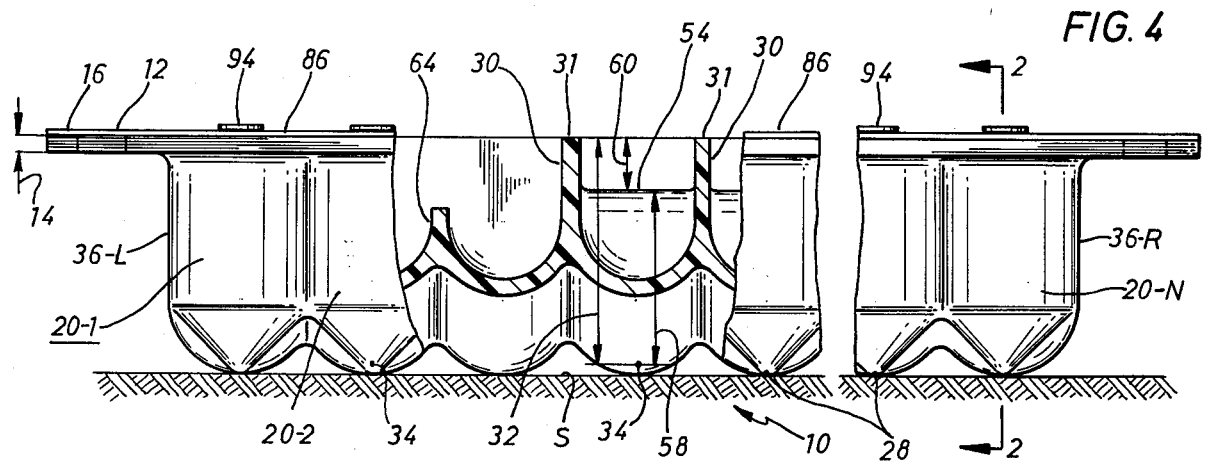
FIG. 4 is a front elevation view of the apparatus shown in FIGS. 1 through 3 showing portions in section along section lines 4—4 in FIG. 2.

With reference to FIGS. 1 through 4, an apparatus generally indicated by reference numeral 10 for testing the effects of an antibiotic, a chemical or biochemical substance in liquid suspension, on an antibiotic or a bacterial or biochemical substance, which apparatus embodies the teachings of this invention, is illustrated.

The apparatus 10 generally includes a substantially planar base portion 12 of a predetermined thickness dimension 14 consistent with the structural stability and integrity of the apparatus 10. The upper surface 16 of the base 12 defines a sealing surface extending about the periphery of the apparatus 10 for receiving a cover, as is made clearer herein. The base 12 is provided with attachment ears 18 disposed at any convenient locations about the periphery of the apparatus 10.

Carried by the base 12 is a plurality N, where N is any convenient number, of side-by-side test chambers or test zones 20-1 through 20-N. The test chambers 20 may be formed in the base 12 in any convenient manner, as by depression of the base 12, and may take any convenient frontal or side cross sectional shape. Shown in FIGS. 1 through 4 is an apparatus of the type most typically utilized to test the effect of a bacterial suspension on a variety of antibiotic substances or on varying concentrations of an antibiotic substance in accordance with the invention. In FIGS. 1 through 4, each test chamber 20 includes a substantially cylindrical portion 22 closed by a lower conical member 24. It is in the lower conical member 24 that the appropriate substance 26, such as an antiobiotic (or varying concentrations of an antibiotic) upon which the bacterial suspension is to be tested is disposed. The substance 26 (as the antibiotic) is in dehydrated form within the test chambers 20. The exterior lower tips 28 of the lower conical volumes 24 serve as a support point for the apparatus 10 on any suitable surface S. Each test chamber 20 is separated and isolated from the next-adjacent test chamber by a side wall 30. The side walls 30 extend upwardly to a planar surface 31 disposed a first predetermined distance 32 above a preselected point 34 within the test zone 20, such as the interior apex of the conical member 24 of the test chambers 20. Of course, the lateral boundaries of the first and the Nth test chambers are defined by end walls 36L and 36R which extend from front to rear at the left and right ends of the apparatus 10, respectively.

Also formed within and carried by the base 12 is a common reservoir 40. The reservoir 40 is defined by the end walls 36, a back wall 38 and a sloped portion 44 leading from the lowermost point 46 within the reservoir 40 upwardly toward the test chambers 20. The exterior of the reservoir 40 opposite the point 46 defines a contact point 48 which cooperates with the external tips 28 of the test chambers 20 to maintain the apparatus 10 in a stable supported relationship with the surface S. For later reference purposes, an axis 50 (FIGS. 2 and 3) extends longitudinally of the apparatus 10 through the reservoir 40.

The sloped portion 44 of the reservoir 40 defines a downwardly curved transition region 54 adjacent the test chambers 20 and thereby serves to define a barrier between each of the test chambers 20 and the common reservoir 40. As seen from the Figures, as measured with respect to the reference point 34 in the test chambers, the height of the barrier extends a second predetermined distance 58 between the reference point 34 and the top of the curved transition region 54. The distance 58 is less than the distance 32. It may therefore be appreciated that a clearance gap 60 is defined between the top of the curved transition region 54 atop the sloped portion 44 of the reservoir and a horizontal datum containing the planar top surfaces 31 of each side wall 30. The horizontal datum also contains the upper surface 16 of the base 12.

Disposed within the reservoir 40 is an array of guide walls 64. If N test chambers 20 are disposed within apparatus 10, it is clear that the array of guide walls 64 includes (N-1) guide walls. The guide walls 64 extend upwardly from the sloped portion 44 of the reservoir 40 and are merged at their upper ends 66 into the side walls 30 between each of the test chambers 20. In FIGS. 1 through 4, it is noted that the merger of the upper ends 66 of the guide walls 64 into the side walls 30 occurs in the vicinity of the curved transition region 54 between the reservoir 40 and the test chambers 20. The upper surfaces 67 of the guide walls 64 in the vicinity of the merger are coplanar with the surfaces 31 of the side walls 30. The lower end 68 of each of the guide walls 64 forms a planar shelf 70 spaced a predetermined distance 72 above the reference point 46 disposed within the reservoir 40. The axes 74 (FIG. 2) of the guide walls extend substantially perpendicularly to the axis 50 of the apparatus 10. In the embodiment of the apparatus shown in FIGS. 1 through 4, the portion of the guide walls 64 intermediate the upper surface 67 thereof adjacent the point of merger into the side walls 30 and the lower shelf 70 is inclined substantially parallel to the sloped portion 44 of the reservoir 40.

As seen in FIGS. 1 through 4, each of the guide walls 64 cooperates with the next-adjacent guide wall (or, in the case of the first and last guide wall, with the end walls 36L and 36R, respectively) to define an array of N channels 80. Each channel 80 is associated with one of the test chambers 20 to channelize a flow of liquid having the substance under test therein from the reservoir into each of the test chambers 20. In this manner, the natural tendency of the liquid to seek a level adjacent one of the end walls 36 as the apparatus is rotated is avoided, and the introduction of liquid into each of the test chambers 20 is insured.

In the preferred form of the invention, the planar base, end walls, back wall, test chambers, side walls, reservoir and guide walls are each integrally fabricated, using an injection molding process, of a suitable clear plastic material, as crytal polystyrene of sufficient thickness 14 to insure structural integrity. Of course, any other suitable manufacturing expedient or materials may be utilized to construct apparatus having the structural relationships of the elements defined above. Moveover, whereas integration of the structural elements as discussed above is preferred, apparatus in which any of the various structural elements are separate one from the other and secured together in the manner described above is construed to fall within the contemplation of this invention.

A clear plastic cover 86 is provided overlying the upper surface 16 of the base 12 and contacting on its inner surface the upper surfaces 31 of the side walls 30 and the upper surfaces 67 of the guide walls 64 in the vicinity of their merger to the side walls. The cover 86 is attached by any suitable means, preferably ultrasonic welding. With the cover 86 in place, it may be appreciated that each test chamber 20 communicates with the reservoir 40 only through the clearance 60 defined between the curved transition region 54 defining the barrier and the inner surface of the plastic cover 86. The plastic cover is provided with a re-sealable opening 88 having a detachable cap 90 thereof. Further, access to each of the test zones 20 may be effected through an array of N openings 92 provided in the cover 90 above each test chamber 20. The openings 92 are re-sealably covered by caps 94.

It is often necessary to ascertain the effect that a given antibiotic or a selected concentration of antibiotic would have on a bacterial substance. It is in such testing that the apparatus shown in FIGS. 1 through 4 is primarily (though not exclusively) utilized. In operation, the liquid containing the in suspension the bacterial or biochemical substance upon which the effect of an antibiotic or concentration thereof is to be ascertained is introduced into the reservoir 40 through the opening 88 provided in the cover 86. The liquid suspension is introduced into the reservoir 40 to a height just above the height of the upper surface of the shelf 70. The cap 90 is then replaced over the opening 88 and the apparatus 10 rotated on an axis of rotation parallel to or coincident with the axis 50. The channels 80 defined by the guide walls 64 cooperate to conduct the liquid suspension introduced into the reservoir into the test chambers 20 with which they are associated upon rotation of the apparatus such that even if the apparatus is inadvertently tilted during the rotation thereof liquid suspension to be tested is nevertheless conducted by the channels 80 into the appropriate test chamber 20. In this manner, a liquid containing a suspension of a substance to be tested is introduced into each of the test chambers 20 so that the effect of each of the antibiotics disposed within the test zones may be ascertained.

In FIGS. 5 and 6, shown is a slightly modified embodiment of the invention found particularly useful in connection with the testing of a bacterial substance in suspension on a variety of biochemical substances disposed within the test chambers 20 for the purpose, e.g., of determining the identity of the bacteria in suspension. In the embodiment of FIGS. 5 and 6 it may be observed that each of the test chambers 20' comprises a flattened rectangular portion 95 wherein the chemical substance 26 is disposed. With this structure, the base 12' is therefore provided with an upstanding leg 96, which extends below the base to an exterior point 97 to thereby cooperate with the points 48 to support the apparatus on the surface S. Further, in the modification shown in FIGS. 5 and 6, the upper surfaces 67' of each of the guide walls 64 remain coplanar with the upper surface 31 of the side walls 30 for a further distance toward the back wall 38, the inclined portions thereof extending between a step 98 disposed in the vicinity of the center of the reservoir 40 toward the lower end 68 to provide an enhanced channel effect. The inclined portion of the guide walls are substantially parallel to the sloped portion of the reservoir. The base 12 is provided with suitable hanging openings 18' for reception by a suitable tray or the like to thereby permit the apparatus to be supported in a vertically upright position (perpendicular to the suface S) if desired.

In view of the foregoing it may be appreciated that apparatus in accordance with this invention provides an array of guide walls disposed within the reservoir adapted to cooperate with each other (or with the appropriate end walls) to define an array of channels whereby a liquid suspension introduced into the reservoir may be conducted therefrom into each of the test chambers by rotation of the apparatus about an axis of rotation parallel to or coincident with the axis of the reservoir. In this manner, the natural tendency of liquid to seek its own level as a result of indadvertent tilting or canting of the apparatus during rotation thereof is avoided and liquid is conducted through the channels defined between the guide walls into each of the test chambers to effectively introduce the liquid into each of the test chambers.

Having defined a preferred embodiment of the invention, those skilled in the art may effect numerous modifications thereto in view of the foregoing description, which modifications lie within the scope of this invention as defined in the appended claims.

What is claimed is:

1. In an apparatus for testing the effects of an antibiotic or chemical on bacterial or biochemical substances, said apparatus being of the type having:
   (a) a plurality of side-by-side test chambers each adapted to receive therein a bacterial or biochemical substance, each test chamber being separated from the next-adjacent test chamber by a side wall;
   (b) a common reservoir disposed adjacent each of the test chambers, the reservoir being separated from each of the test chambers by a barrier having a height less than the height of the side walls, the reservoir having an axis of rotation extending therethrough;
   wherein the improvement comprises:
   an array of guide walls disposed within the reservoir, each guide wall merging into one of the side walls and cooperating with its next-adjacent guide wall to define an array of channels, each channel communicating with one of the test chambers and each adapted to channelize a liquid disposed in the reservoir into the test chamber with which it is associated upon rotation of the apparatus about the axis of rotation such that a flow of liquid is maintained from the reservoir to each test chamber even if the apparatus is tilted during rotation thereof about the axis of rotation.

2. Apparatus according to claim 1 further comprising:
   a cover disposed over the test chambers and the reservoir, the cover having an inlet aperture therein, the upper surfaces of each of the side walls and a portion of each of the guide walls being contacted against the inner surface of the cover, the barrier being spaced a predetermined clearance distance from the cover such that the reservoir communicates with each test chamber through the clearance, liquid being introducable into the reservoir through the inlet aperture in the cover.

3. Apparatus according to claim 2 wherein the guide walls are parallel with each other.

4. Apparatus according to claim 2 wherein each guide wall inclines from its point of contact with the cover toward a substantially planar shelf portion, the upper surface of each shelf portion of each guide wall being disposed above the lowermost point in the reservoir.

5. Apparatus according to claim 4 wherein the reservoir includes an inclined surface leading from the lowermost point in the reservoir toward the barrier, and wherein each guide wall slopes from its region of merger with its associated side wall toward a lower shelf portion at an incline substantially parallel to the inclined surface of the reservoir, the upper surface of each shelf portion being disposed above the lowermost point in the reservoir.

6. Apparatus according to claim 4 wherein the point of contact of each guide wall to the cover lies above the barrier.

7. Apparatus according to claim 6 wherein the guide walls are parallel with each other.

8. Apparatus according to claim 4 wherein the point of contact of each guide wall to the cover lies above the center of the reservoir.

9. Apparatus according to claim 8 wherein the guide walls are parallel with each other.

10. Apparatus according to claim 2 wherein the test chambers, side walls, reservoir, and guide walls are each integrally fabricated by injection molded from a plastic material and wherein the cover is attached by ultrasonic welding.

11. Apparatus according to claim 10, wherein the plastic material is crystal polystyrene.

12. Apparatus according to claim 1 wherein the test chambers, side walls, reservoir and guide walls are each integrally fabricated by injection molding from a plastic material.

13. Apparatus according to claim 12 wherein the plastic material is crystal polystyrene.

14. Apparatus according to claim 1 wherein each guide wall inclines from its region of merger with its associated side wall toward a substantially planar shelf portion, the upper surface of each shelf portion of each guide wall being disposed above the lowermost point in the reservoir.

15. Apparatus according to claim 1 wherein the reservoir includes an inclined surface leading from the lowermost point in the reservoir, and wherein each guide wall slopes from its region of merger with its associated sidewall toward a lower shelf portion at an incline substantially parallel to the inclined surface of the reservoir, the upper surface of each shelf portion being disposed above the lowermost point in the reservoir.

16. Apparatus according to claim 15 wherein the guide walls are parallel with each other.

17. Apparatus according to claim 15 wherein the guide walls are parallel with each other.

18. Apparatus according to claim 1 wherein each guide wall has an upper surface substantially coplanar with the upper surface of its associated side wall, the upper surface of each guide wall extends from the region of merger to generally the center of the reservoir, each guide wall sloping from the edge of the upper surface toward a lower shelf, the surface of the shelf being disposed above the lowermost point in the reservoir.

19. Apparatus according to claim 18 wherein the reservoir includes an inclined surface leading from the lowermost point in the reservoir and wherein the sloped surface of each guide wall is inclined substantially parallel to the inclined surface of the reservoir, step being defined between the upper surface of each guide wall and the sloped surface thereof.

20. Apparatus according to claim 1 wherein the guide walls are parallel with each other.

21. A method for testing the effects of an antibiotic or chemical on bacterial or biochemical substances comprising the steps of:
 introducing a liquid suspension containing an antibiotic or chemical to be tested into a common reservoir of a test apparatus until the level liquid in the reservoir lies above the lower end of an array of guide walls disposed within the reservoir;
 rotating the apparatus about an axis of rotation to cause a channelized flow of liquid from the reservoir into each of a plurality of test chambers disposed in fluid communication with the reservoir; and
 observing each of the plurality of test chambers to test the affects of the antibiotic or chemical on the bacterial or biochemical substances.

* * * * *